United States Patent
McAuliffe et al.

(10) Patent No.: US 10,729,372 B2
(45) Date of Patent: Aug. 4, 2020

(54) SENSOR FOR AN ORAL APPLIANCE (71) Applicant: THE PROVOST, FELLOWS, FDN SCHOLARS, & THE OTHER MEMBERS OF BOARD, OF THE COLLEGE OF THE HOLY & UNDIV. TRINITY OF QUEEN ELIZABETH, NEAR DUBLIN, Dublin (IE)

(72) Inventors: Padraig Martin McAuliffe, Cratloe (IE); James Joseph Doyle, Dublin (IE); Ramesh Babu Padamati, Dublin (IE); Dermot Joseph Sullivan, Dublin (IE); Paul Phillips, Donaghadee (GB); Brian Christopher O'Connell, Dublin (IE)

(73) Assignee: The Provost, Fellows, Foundation Scholars & The Other Members of Board, of the College of the Holy & Undiv. Trinity of Queen Elizabeth, Near Dublin, Dublin (IE)

( * ) Notice: Subject to any disclaimer, the term of this patent is extended or adjusted under 35 U.S.C. 154(b) by 774 days.

(21) Appl. No.: 15/026,910

(22) PCT Filed: Oct. 1, 2014

(86) PCT No.: PCT/EP2014/071101
§ 371 (c)(1),
(2) Date: Apr. 1, 2016

(87) PCT Pub. No.: WO2015/049321
PCT Pub. Date: Apr. 9, 2015

(65) Prior Publication Data
US 2016/0242692 A1  Aug. 25, 2016

(30) Foreign Application Priority Data
Oct. 2, 2013 (GB) .................................. 1317478.4

(51) Int. Cl.
*A61B 5/00* (2006.01)
*A61B 5/22* (2006.01)
(Continued)

(52) U.S. Cl.
CPC ............ *A61B 5/4557* (2013.01); *A61B 5/038* (2013.01); *A61B 5/228* (2013.01); *A61B 5/4542* (2013.01);
(Continued)

(58) Field of Classification Search
CPC ...... A61B 5/4542–4557; A61B 5/6847; A61B 5/038; A61B 5/682; A61B 5/228; A61F 5/566; A61F 2005/563
See application file for complete search history.

(56) References Cited

U.S. PATENT DOCUMENTS 4,629,424 A    12/1986  Lauks et al.
6,089,864 A *  7/2000  Buckner .................. A61F 5/56
                                                       433/6
(Continued)

FOREIGN PATENT DOCUMENTS

WO    WO 2015/049321 A2    4/2015

OTHER PUBLICATIONS

International Search Report, for International Appl. No. PCT/EP2014/071101, dated Apr. 24, 2015, consisting of 5 pages, entitled "A Sensor For an Oral Appliance."

*Primary Examiner* — Sean P Dougherty
*Assistant Examiner* — David Joseph Fernandez-Fidalgo
(74) *Attorney, Agent, or Firm* — Hamilton, Brook, Smith & Reynolds, P.C.

(57) ABSTRACT

The invention provides a sensor assembly embeddable within an oral appliance comprising a sensing means; and a data processing means coupled to the sensing means for processing data obtained by the sensing means; wherein the
(Continued)

sensing means and the data processing means are sealed within a deformable layer.

26 Claims, 7 Drawing Sheets

(51) Int. Cl.
*G06F 30/00* (2020.01)
*A61B 5/03* (2006.01)
*A61F 5/56* (2006.01)

(52) U.S. Cl.
CPC ............ *A61B 5/682* (2013.01); *A61B 5/6847* (2013.01); *A61F 5/566* (2013.01); *G06F 30/00* (2020.01); *A61B 5/0002* (2013.01); *A61B 2562/12* (2013.01); *A61F 2005/563* (2013.01)

(56) References Cited

U.S. PATENT DOCUMENTS

2007/0235231 A1* 10/2007 Loomis .................... G01L 1/205
  178/18.06
2012/0172677 A1* 7/2012 Logan .................... A61B 5/082
  600/301

\* cited by examiner

| Sample | Average Youngs Modulus (MPa) | Average Ultimate Tensile Strength (MPa) | Average Percentage Strain at Break (%) | Average Toughness (MJ/m$^3$) | Yield Point (MPa) |
|---|---|---|---|---|---|
| Linear low-density polyethylene (Sigma Aldrich) | 160 | 29 | 1222 | 205 | 9 |
| Elvax 3130 | 36 | 17 | 1000 | 100 | 5 |
| Elvax 470a | 22 | 20 | 1000 | 116 | 4 |
| Elvax 40L03 | 2 | 6 | 1400 | 40 | 1 |
| EXACT 0201 | 45 | 31 | 1200 | 183 | 6 |
| Pebax 2533 | 7 | 19 | 1500 | 147 | 2 |
| Pebax 3533 | 13 | 19 | 1370 | 140 | 3 |
| Pebax 4033 | 44 | 27 | 970 | 163 | 7 |
| Pebax 5533 | 90 | 40 | 990 | 240 | 14 |
| Pebax 2533:3533 (1:1) | 11 | 13 | 1030 | 78 | 2 |
| Pebax 2533:4033 (1:1) | 19 | 20 | 940 | 116 | 5 |
| Pebax 3533:2533 (2:1) | 13 | 18 | 1180 | 115 | 3 |
| Pebax 2533:4033 (2:1) | 14 | 18 | 1000 | 118 | 4 |
| Pellethane 2363 90AE | 24 | 52 | 1014 | 251 | 5 |
| Tecoflex EG-65D | 260 | 59 | 524 | 170 | 15 |
| PVC Apex B85NT | 11 | 22 | 327 | 43 | 0.3 |
| Polycyclooctene (0.5% Dicumylperoxide) | 73 | 15 | 909 | 89 | 0.9 |
| Polycyclooctene (1% Dicumylperoxide) | 73 | 11 | 743 | 60 | 0.8 |
| Polycyclooctene (1.5% Dicumylperoxide) | 63 | 12 | 799 | 67 | 0.7 |
| Polycyclooctene (2% Dicumylperoxide) | 85 | 12 | 792 | 63 | 0.5 |
| Lotader 8900 | 3.8 | 5.6 | 1197 | 41 | 1.3 |
| Lotader 8900: Beeswax (80:20) | 2.3 | 5.5 | 718 | 24 | 1.2 |
| Lotader 8900: Beeswax (40:26) | 2.6 | 4.6 | 570 | 16 | 1.0 |
| Lotader 8900:PHA (5%) | 3.5 | 5.3 | 647 | 23 | 1.1 |
| Lotader 8900:PHA (10%) | 3.1 | 5.4 | 615 | 22 | 0.9 |
| Lotader 8900:PHA (15%) | 2.5 | 3.7 | 592 | 15 | 0.8 |

Figure 7

SENSOR FOR AN ORAL APPLIANCE

This application is the U.S. National Stage of International Application No. PCT/EP2014/071101, filed Oct. 1, 2014, which designates the U.S., published in English, and claims priority under 35 U.S.C. §§ 119 or 365(c) to GB Application No. 1317478.4, filed Oct. 2, 2013. The entire teachings of the above applications are incorporated herein by reference.

FIELD OF THE INVENTION

The present invention is concerned with oral appliances for use in the prevention, detection and monitoring of bruxism (the grinding of teeth). More particularly, the present invention is concerned with providing a sensor which can be integrated into an oral appliance in order to detect and monitor bruxism, as well as an oral appliance suitable for use with such a sensor.

BACKGROUND TO THE INVENTION

Bruxism is a common dental problem which when undiagnosed or poorly managed for a long period of time can cause very significant cosmetic and functional dental problems and lead to great expense on dental treatment. In fact, bruxism is one of the greatest risks to the longevity of teeth and almost all types of dental treatment. It has been found that veneers fail seven times faster and crowns fail two to three times faster in the mouth of a bruxer compared to normal patients. Dental implants are almost twice as likely to have complications in tooth grinders. Aside from expensive treatments, fractures of parts of teeth are a very common cause of fillings and root canal treatments, on which many tens of billions are being spent each year. Many of these treatments are paid for by insurance companies and would be avoidable if bruxism were better managed.

Splints are highly effective at preventing tooth wear/fractures and facial pain—so long as they are used. Many types of splints exist, and these can be fabricated from hard or soft polymer or a combination of multi-layered, polymer-based mouth guard materials. One type of known splint is a hard/soft splint. Conventional hard/soft splint designs have a soft layer comprising a top surface, a bottom surface and two side surfaces. The bottom surface of the soft layer is adapted to be in contact with the teeth the splint is fitted on, while the top surface of the soft layer is coupled to a hard outer layer. The hard outer layer is adapted to be in contact with the opposing teeth and protects against the high force effects of bruxism. The two side surfaces of the soft layer are thus left exposed when positioned in the mouth of a user. In current use, these splints are usually made by a thermoforming process. A bilayered hard and soft sheet or foil is heated to a temperature where it can easily be adapted by pressure or a vacuum around a stone model of the mouth. Once adaption is complete, the excess foil is trimmed and shaped into an acceptable splint shape and delivered to the patient. Another type of splint is a hard splint. A hard splint can be fabricated using many techniques. One typical fabrication technique is through the use of heat-processed PMMA, with the splint cast in a lost wax process. Another fabrication technique is where the hard splint is built up directly on a model using PMMA monomer and polymer powder, known as the "salt and pepper" technique. A further type of hard splint is made by adapting light cured material, in unpolymerised form, either directly to the teeth intra-orally, or to a model of the teeth, and then light curing the material.

There are a number of problems associated with existing splints. Firstly, they tend to be bulky, and as a result about 50% of patients stop using them after 12 months, even though many dentists recommend that they be used for life. Most patients will continue to grind their after ceasing splint use. As a result, many patients presenting with severe bruxism-related problems report having tried a splint for a short time but gave up using it. While bruxism persists over many years in most patients, for some it is a temporary problem, possibly related to a stressful time of life. For these cases, lifelong splint use is not required, yet many dentists will recommend replacing splints every 2 to 3 years, and thus burdening patients with the associated expense involved in buying a replacement splint.

Accordingly, there are a number of issues encountered by dentists with treating bruxism. In particular, it can be difficult to establish when to prescribe splints, how to monitor splint effectiveness and patient compliance with the use of the splint, as well as when it should be recommended that splint use be discontinued. Therefore, because of the lack of a means of objectively monitoring bruxism over time, many patients who need splints are not using them and many patients who do not need splints are wasting money on them.

There have been a number of devices which have been developed in an attempt to address these issues. Some of these devices have been designed to detect bruxism in a patient. One such known device is based on an experimental method (EMG) of monitoring activity in the muscles involved in chewing. It comes as a single use adhesive pad, which attaches to the side of the face and measures the presence/absence and the severity of bruxism over the course of 24 hours. However, this device only lasts for 24 hours and is relatively expensive to buy. If the patient doesn't grind on the night of use (which is at least 25% likely), then false negatives are unavoidable. It also can take at 2 weeks to establish a meaningful pattern. Furthermore, it has been found that the EMG monitoring of bruxism is very heavily contaminated with artefacts, making reliable automated bruxism diagnosis very difficult.

Other known devices have been developed to reduce bruxism intensity. One such device consists of an electrode that detects activity in the chewing muscles during bruxism. Once activity in these muscles exceeds a certain threshold, the device delivers a small electric shock to the muscle which is intended to reduce bruxism intensity. However, it is uncertain that the effects on bruxism activity are sustained in the long-term, and the device is very cumbersome to use during sleep. Also, there are broader health concerns about this approach related to disturbance of sleep. In addition, a splint is still recommended, as the shock therapy only reduces the bruxism activity.

Other devices have been developed to determine whether a splint is being used by a patient. One known such device integrates into a splint, and uses temperature monitoring to determine whether the splint is being used by a patient. However, it does not monitor actual bruxism activity in any way. Therefore it has no diagnostic capability whatsoever and only monitors compliance, without the capacity to reinforce it with personalised feedback on the severity of the condition. It also offers no direct evidence to patients that they are still grinding and therefore no reason to believe that splint use is still needed.

Another known device measures how a splint flexes under biting. It comprises a sensor strip which is easily integrated with the outer surface of a splint, rather than inside the normal splint contour. As a result, this device is very bulky. In addition, it cannot be used in the cheaper "boil and bite"

splints or in the hard-soft type splints. It also typically lasts for only 6 months and cannot be recharged. A further drawback of this device is that a patient has to visit the dentist to have the data downloaded. As a result, no on-going compliance reinforcement can happen. In addition, the device must be used with a base station, which must be worn around the neck or in a pocket at night.

There are also some patent applications which have attempted to address many of the problems mentioned above. These include International Patent Publication Nos. WO 2010/023655, WO 2000/44284, WO 2006/068896 and WO 2011/091355, as well as U.S. Pat. No. 5,078,153 and US Patent No. 20133/211270 and German Patent Application No. DE 102004043665.

It will be appreciated therefore that all of the devices developed to date in an attempt to address the issues related to bruxism detection and monitoring suffer from different drawbacks. As a result, there is currently no accurate, easy to use and long lasting device that successfully overcomes all of the above mentioned issues.

SUMMARY OF THE INVENTION

According to the invention there is provided, as set out in the appended claims, a sensor assembly embeddable within an oral appliance comprising:
a sensing means; and
a data processing means coupled to the sensing means for processing data obtained by the sensing means;
wherein the sensing means and the data processing means are sealed within or positioned on a deformable layer, wherein the deformable layer is adapted to be stretched to fit different dental arch shapes and sizes.

By adapting the deformable layer to be stretched to fit different dental arch shapes and sizes, it ensures that the sensor assembly can be located in each user's mouth so as to provide optimal sensor performance. In addition, it enables the same size sensor assembly to be used in many different shaped mouths, by stretching the deformable layer to accommodate the shape of an individual mouth.

In another embodiment there is provided a splint comprising:
a first layer comprising a top surface, a bottom surface and two side surfaces, the bottom surface adapted for making contact with a first row of teeth of a user when the splint is positioned within the mouth of a user;
a second layer coupled to the first layer for making contact with a second row of teeth of a user, wherein the second layer is harder than the first layer; and
a sensor embedded between the first and the second layers;
wherein the second layer is coupled to the top surface and the side surfaces of the first layer such that the second layer extends over all surfaces of the first layer which are not in contact with the teeth of a user when the splint is positioned in the mouth of a user.

By providing an excess of hard layer extending over the perimeter of the soft layer, it provides mechanical bracing that prevents shear stress on any adhesive which may be used to bond the two layers together and provides for a more optimal adhesive layer thickness. It also transfers a greater amount of the bite force to the sensor. In addition, it facilitates reproducible assembly of the two layers together, and thus ensures that any sensor placed in between the hard and soft layers maintains a stable resting resistance. Furthermore, as the joint between the hard and soft layers faces inward, it is considerably more difficult to separate the two layers apart than is the case for conventional hard/soft splint designs.

In another embodiment there is provided method of fabricating a splint into which a sensor is to be embedded, the method comprising the steps of:
forming a first layer comprising a top surface, a bottom surface and two side surfaces, the bottom surface for making contact with a first row of teeth when the splint is positioned within the mouth of a user;
adhering a deformable or stretchable template of the sensor to be embedded in the splint to the surface of the first layer at the position where the sensor is to be located in the splint;
removing the sensor template so as to provide a cavity into which the sensor can be embedded into the splint; and
coupling a second layer to the first layer, the second layer for making contact with a second row of teeth, wherein the second layer is harder than the first layer;
wherein the second layer is adapted to be coupled to the top surface and the side surfaces of the first layer such that the second layer extends over all surfaces of the first layer which are not in contact with the teeth of a user when the splint is positioned in the mouth of a user.

In another embodiment there is provided a sensor assembly embeddable within an oral appliance comprising:
a sensing means; and
a data processing means coupled to the sensing means for processing data obtained by the sensing means;
wherein the sensing means and the data processing means are sealed within a deformable layer.

In one embodiment the deformable layer comprises a stretchable polymer film.

In one embodiment the polymer film is adapted to exhibit a low yield strength and an extended plastic deformation region under increasing strain.

In one embodiment the polymer film is fabricated from one or a combination of: a polyether block amide polymer, polyurethane, polyethylene, polyolefin, polyvinylchloride, polypropylene, polystyrene, elastomer polymer, silicone, terpolymer, reactive polyolefin, plastomer, natural polymer, rubber, biodegradable polymer, biopolymer, inorganic polymer, shape memory polymer, thermoset polymers and a thermoplastic polymer.

In one embodiment the deformable layer is stretched via a shape memory process.

In one embodiment the film further comprises additives added to the polymer to control the properties of the film.

In one embodiment the additives comprise one or more of: waxes, organic or inorganic clays, organic or inorganic nanotubes, organic or inorganic nanowires, organic or inorganic nanoparticles, organic or inorganic particles, organic or inorganic spheroids, organic or inorganic tubes, organic or inorganic wires, ceramics, organic or inorganic fibres, silica, mica or glass forms.

In one embodiment the film comprises a top layer and a bottom layer, wherein the sensing means and the data processing means are sealed between the top layer and the bottom layer.

In one embodiment wherein the polymer film comprises a top layer and a bottom layer, wherein the sensing means and the data processing means are sealed between the top layer and the bottom layer.

In one embodiment the top layer is sealed to the bottom layer by one of: chemical adhesion, heat welding, sonic welding, light irradiation, or any method to cure or partially cure the polymer layer in-situ and tailoring surface tension on one or multiple layers, or via pressure sensitive tack where a degree of bond is formed between the two layers upon brief contact. This can occur between two materials which surfaces are tacky to touch, including viscoelastic polymers, via cohesive interaction, surface micro-structured or surface nano-structured films and/or with uncross-linked or lightly cross-linked polymer above the glass transition temperature.

In one embodiment the top layer is sealed to the bottom layer by chemical adhesion, wherein the characteristics of the chemical adhesive are adapted so as to optimise the performance of the sensing means.

In one embodiment the sensing means comprises a plurality of pressure sensors for detecting oral pressure activity.

In one embodiment the deformable layer is adapted to deform such that the plurality of pressure sensors can be aligned along the dental arch of a user when the sensor assembly is positioned within the mouth of a user.

In one embodiment the deformable layer is indented between at least two adjacent pressure sensors.

In one embodiment each pressure sensor comprises:
a polymer composite material comprising a polymer mixed with an electrically conductive material.

In one embodiment the composition of the electrically conductive material is adapted to provide accurate sensor data under low and high pressure.

In one embodiment the electrically conductive material comprises a metal and/or a carbon based material.

In one embodiment the electrically conductive material takes the form of one of: tubes, wires, fibres, spheroids, sheets, beads or matting.

In one embodiment the loading of the electrically conductive material is between 0.001-50% wt.

In one embodiment each pressure sensor has a resistance at rest of >=1 kΩ.

In one embodiment each pressure sensor is configured to provide a shore hardness within the range of 30D-80D.

In one embodiment the polymer comprises one of: electrically conductive polymers, piezoelectric polymers, elastomers, plastomers, and urethane-based, ethylene-based, styrene-based, nylon-based, amide-based, nitrile-based, vinyl-based, propylene-based, acrylic-based and siloxane-based polymer composites.

In one embodiment the sensing means is coupled to the data processing means by a conducting means.

In one embodiment the conducting means comprises two electrically conductive electrodes between which the sensing means is positioned.

In one embodiment the length of the conducting means is adapted to co-operate with all configurations of the deformable layer.

In one embodiment the data processing means comprises a data storage means and a wireless transmitter for transferring the data to an external receiver.

In one embodiment the deformable layer comprises at least one detachable segment.

In another embodiment there is provided a splint comprising:
a first layer for attachment to a first row of teeth when the splint is positioned within the mouth of a user;
a second layer coupled to the first layer for making contact with a second row of teeth, wherein the second layer is harder than the first layer; and
a sensor embedded between the first and the second layers; wherein the first layer comprises a top surface, a bottom surface and two side surfaces and wherein the second layer is coupled to the first layer at its top surface and its two side surfaces.

In one embodiment one of the layers comprises one or more grooves, and the other layer comprises one or more notches or indentations, and wherein the coupling of the two layers further comprises the coupling of each notch to its corresponding groove.

In another embodiment there is provided an oral appliance system comprising:
a splint; and
a storage case comprising:
a receiver for receiving data transmitted from the data processing means of the sensor assembly; and
a transmitter for transferring data from the storage case to an external processor;

In another embodiment there is provided a method of fabricating a splint into which a sensor is to be embedded, the method comprising the steps of:
forming a first layer for attachment to a first row of teeth when the splint is positioned within the mouth of a user;
adhering a template of the sensor to be embedded in the splint to the surface of the first layer at the position where the sensor is to be located in the splint based on an estimated position of the occlusal contacts of a second row of teeth when the splint is positioned within the mouth of a user;
coupling a second layer to the first layer, the second layer for making contact with the second row of teeth, wherein the second layer is harder than the first layer; and
removing the sensor template so as to provide a cavity into which the sensor can be embedded into the splint;
wherein the first layer comprises a top surface, a bottom surface and two side surfaces and wherein the second layer is coupled to the first layer at its top surface and its two side surfaces.

In another embodiment there is provided a method of fabricating a splint into which a sensor is to be embedded, the method comprising the steps of:
embedding a template for the sensor into a splint template at the position where the sensor is to be located in the splint;
casting the splint; and
removing the sensor template from the cast splint so as to provide a cavity into which the sensor can be embedded.

In one embodiment the splint template comprises a top surface, a bottom surface and two side surfaces; and wherein the sensor template is embedded into the splint template such that the exposed surface of the sensor template is aligned with the top surface of the splint template and the position of the centre of the sensor template corresponds to where the fabricated splint will make contact with a row of teeth when positioned in a mouth of a user.

In one embodiment the sensor template further comprises a plurality of protrusions adapted to extend beyond the occluso-buccal and palatobuccal angles of the splint template.

In one embodiment the splint template comprises a wax template, and the method further comprises the steps prior to the step of casting the splint of:
positioning the wax template in a mould; and
burning away the wax.

In one embodiment the splint is cast in acrylic, and the method further comprises the steps of:
embedding a sensor in the cavity; and
sealing the embedded sensor in the cast splint with cold cure acrylic.

In another embodiment there is provided a method of generating a computer model of a splint into which a sensor is to be embedded, the method comprising the steps of:
generating a 3D model of the splint;

inserting into the 3D model a template for the sensor to be embedded into a splint fabricated using the computer model; wherein the dimensions of the sensor template are adapted to correspond to the dimensions of the sensor; wherein the 3D model comprises a top surface, a bottom surface and two side surfaces, and wherein the sensor template is inserted into the 3D model at a position such that the exposed surface of the sensor template is aligned with the top surface of the 3D model, and the position of the centre of the sensor template corresponds to where a splint fabricated using the generated computer model will make contact with a row of teeth when positioned in a mouth of a user.

The present invention also provides a method for fabricating a splint for a user incorporating the sensor assembly of the present invention, the method comprising the steps of: laying a first layer of splint material; adapting the deformable layer of the sensing means to fit the size and shape of the dental arch of the user; placing the sensor assembly with the adapted deformable layer onto the first layer; and sealing a second layer of splint material onto the first layer and the sensor assembly.

The splint may be a splint fabricated using the salt and pepper technique. Alternatively, the splint may be a splint fabricated using light and heat cured material.

In one embodiment, the first layer of splint material is laid on a physical model of a mouth of the user.

In another embodiment, the first layer of splint material is laid directly onto the teeth of the user.

In another embodiment there is provided a method for determining when to commence the processing of sensor data obtained from an oral appliance into which a pressure sensor is embedded, the method comprising the steps of: monitoring for a pressure sensor profile associated with the moment at which the oral appliance is placed in the mouth of a user; and commencing the processing of the sensor data upon detection of the pressure sensor profile; wherein the splint will be automatically be switched out of recording mode and into deep sleep if the force signature associated with splint removal is detected.

In another embodiment the method comprises the steps of: transitioning the oral appliance from deep sleep mode into recording mode when placed in the mouth of a user; in which mode sensor data that exceeds a predefined threshold is processed by the oral appliance; and transitioning the oral appliance from recording mode into light sleep mode if no sensor data exceeding a predefined threshold is detected within a predefined period of time; and returning the oral appliance to recording mode upon detection of sensor data that exceeds the predefined threshold.

The present invention also provides a sensor which is deformable. The sensor may be deformable to cover at least a portion of the full mouth arch tooth line. In this embodiment, a conducting means may be provided which is plastically deformable and locatable proximal to the sensor. The length of the conducting means may be adapted to co-operate with all configurations of the sensor.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION OF THE DRAWINGS

The present invention provides a sensor assembly which can be embedded into an oral appliance for use in the detection and/or monitoring of oral pressure activity, primarily bruxism. The present invention also provides a splint suitable for use with such a sensor device and a method of fabricating such a splint.

The sensor assembly of the invention is sealed within a splint or mouth guard, and configured to fit within the mouth of a wearer. This assembly is adapted to monitor any oral activity which results in a biting force being applied between the teeth. The sensor function is based on the ability to detect changes in the resistance of a conductive polymer, resulting from the input of force on said polymer. Through an analysis of the characteristics of this force, a clear distinction can be made between bruxism and non-bruxism biting events or mouth movements. Data can be recorded in real-time, and either stored on-board for downloading at a later time, or immediately transmitted to a base station, which may be contained within the plastic case ordinarily used for mouth guard storage. It could alternatively be transmitted directly to an electronic device—for example a computer, a tablet, a phone or a watch.

Figure 1:
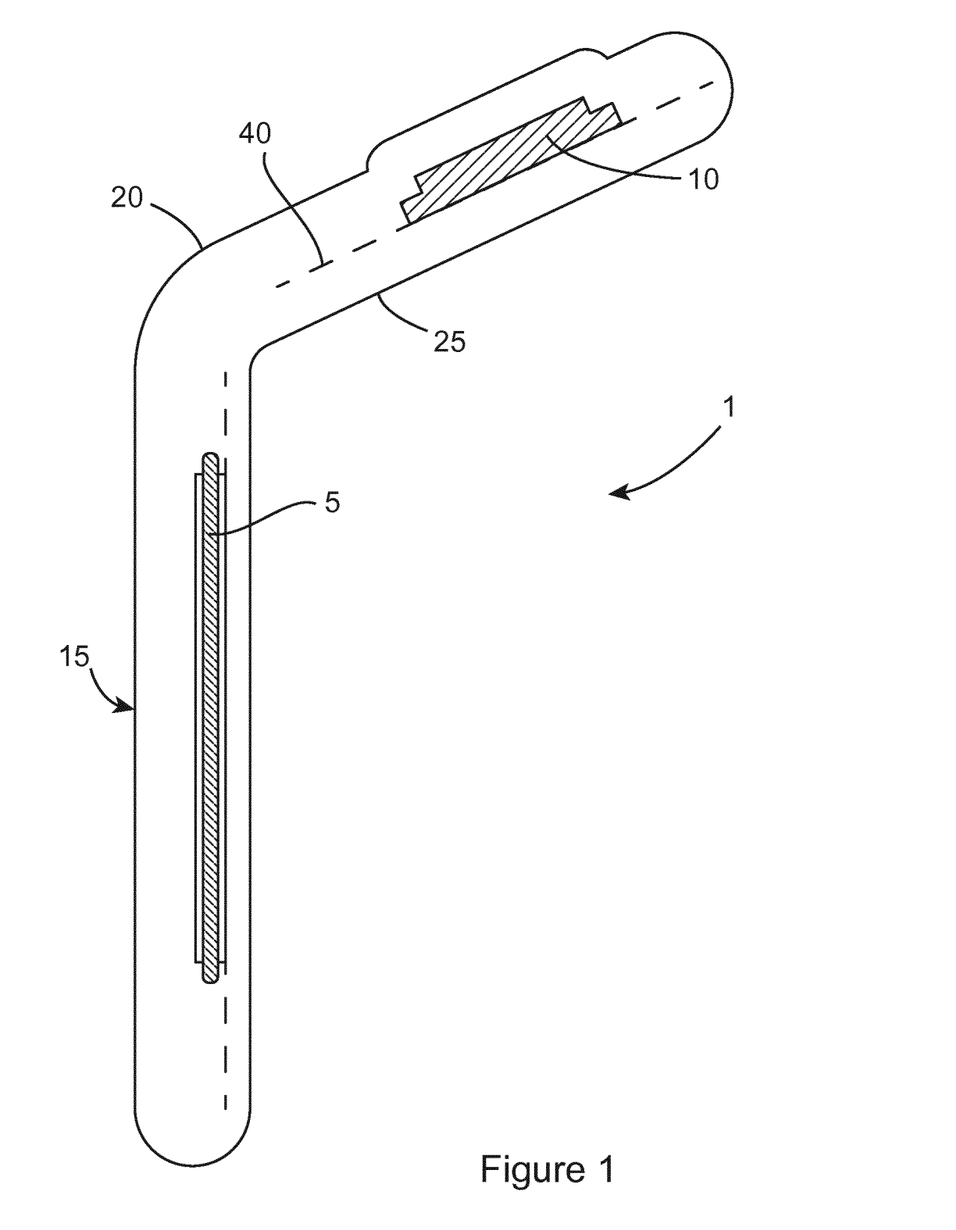
FIG. 1 shows an embodiment of the sensor assembly of the present invention.
Figure 2:
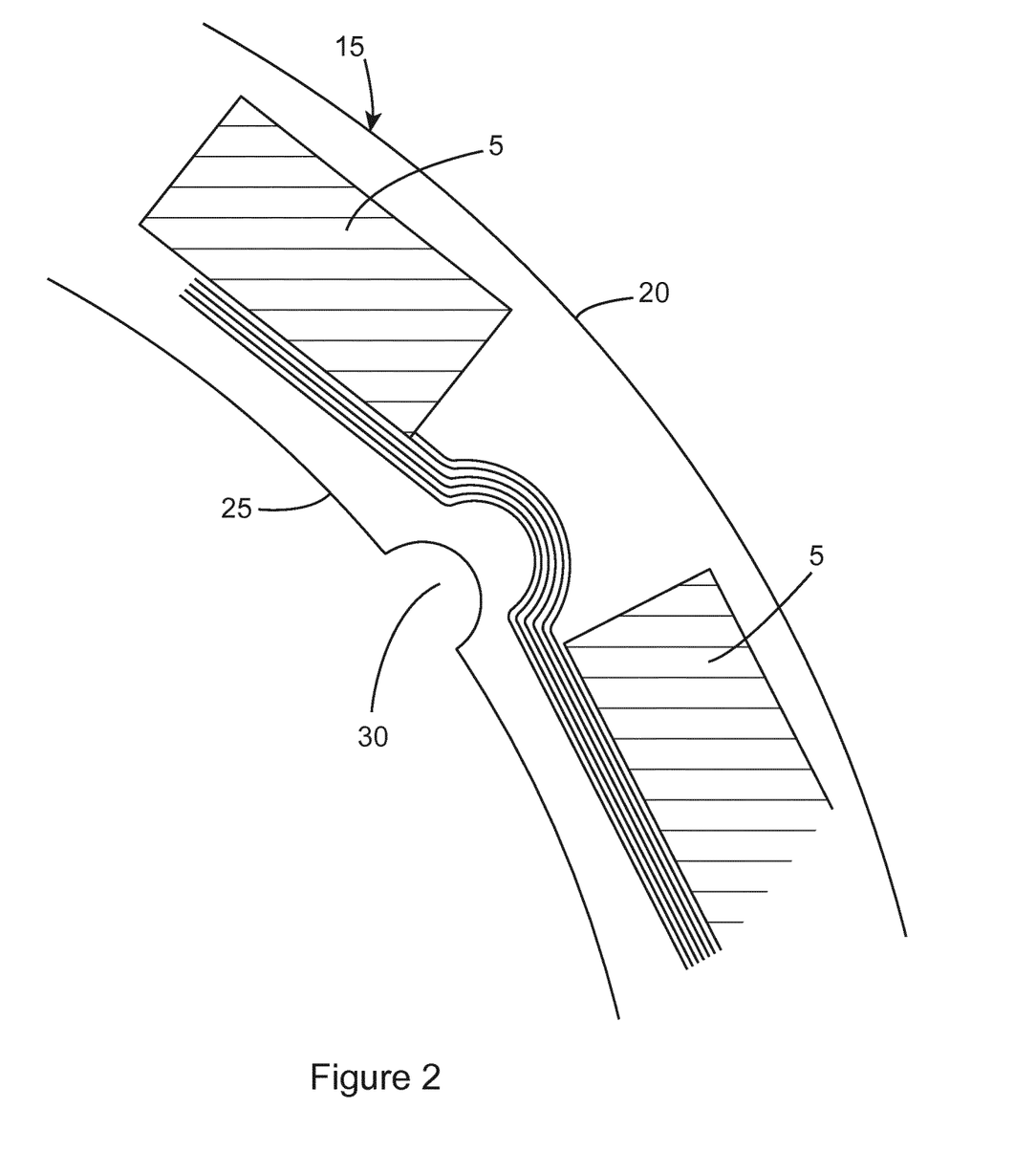
FIG. 2 shows a view of the film of the sensor assembly incorporating indentations.
Figure 3:
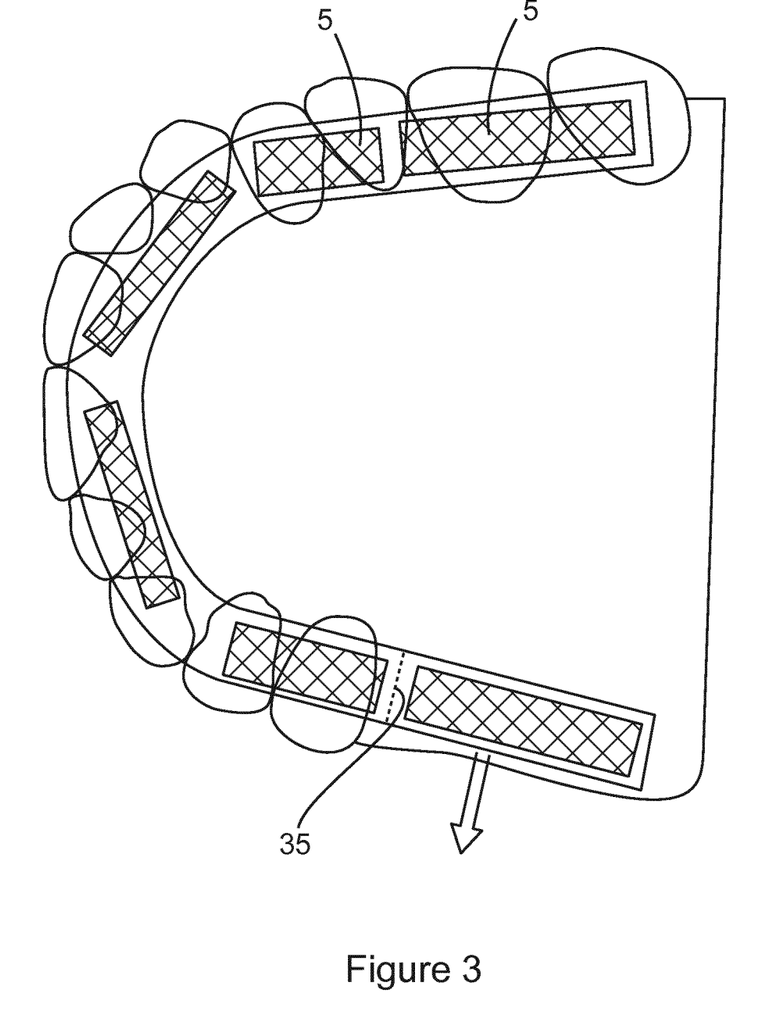
FIG. 3 shows a view of the detachable segments of the sensor assembly.

One embodiment of the sensor assembly of the invention will now be described with reference to FIGS. 1 to 3. The sensor assembly 1 comprises a sensing means 5 and a data processing means 10 coupled to the sensing means. In the described embodiment of the invention, the sensing means take the form of a plurality of thin-film pressure sensors 5 while the data processing means takes the form of a microelectronic circuit 10. The pressure sensors 5 and microelectronic circuit 10 are sealed within a deformable layer, which in the described embodiment comprises a stretchable polymer film coating 15, the dimensions of which can be tailored to fit varying dental arch shapes and sizes. In an alternative embodiment, the pressure sensors 5 could be positioned on the deformable layer instead.

The stretchable polymer film coating 15 is adapted to be easily stretched and fitted to individual dental arch sizes without compromising the output data or any aspect of safety. This ensures that the sensors 5 will fit accurately in the mouth, such that the opposing tooth cusps contact the pressure sensors optimally, in order to maximise the quality and repeatability of the sensor signal. In addition, due to the stretchiness of the film 15, the same size film 15 can be used in many different shaped mouths, by stretching of the film 15 to accommodate the shape of a particular mouth. In one embodiment, the width of the sensors are adapted to be of a size so as to maximise the likelihood of contact with the opposing teeth. Thus, this reduces the level of stretching required for the deformable layer.

Typically the film when stretched to fit the shape of a particular mouth will take the form of a horseshoe, but it will be appreciated that its resting shape is not confined to this. The film 15 comprises a top layer 20 and a bottom layer 25 that are placed above and below the pressure sensor/conductive layers/wires/circuitry.

A plurality of indentations or cut out areas 30 are also provided along the film 15, which allow the stretch to occur with lower force and without the creation of a bump or crease of excess stretched material on the film 15. These cut-out areas 30 also encourage a naturally curved directionality to the stretch as appropriate. In the described embodiment of the invention, the positions of these indentations for a full arch sensor are typically (but not limited to) the midline and the distal surface of lateral incisor or the mesial surface of the canine. However, it will be appreciated that in other embodiments of the invention, the number of indentations may be increased. In addition, the wires connecting the individual sensors to the circuitry are adapted to fold into these areas to avoid their rigidity presenting an impediment to the stretch of the sensor assembly 1.

The stretchable film 15 comprises a polyether block amide film which can be irreversibly or "plastically" elongated during stretching, at temperatures between −30-70 C with a thickness ranging from (0.001-2) mm. Plastic deformation or elongation may be accompanied by an elongation of the host polymer chain and lead to a degree of molecular orientation in a manner known as cold drawing. This film may also be fabricated from one or more of various polyether block amide polymer grades and also various elastomer polymers, silicones, polyolefins, plastomers, terpolymers, reactive polyolefins, shape memory polymers, thermoset polymers and all non-brittle thermoplastic polymers, including all possible blends and copolymers. In one embodiment of the film, additives are added to the polymer composition in order to control the resulting film properties. These additives may include for example waxes, organic or inorganic clays, organic or inorganic nanotubes, organic or inorganic nanowires, organic or inorganic nanoparticles, ceramics, organic or inorganic fibres, silica, mica, glass forms.

Figure 7:
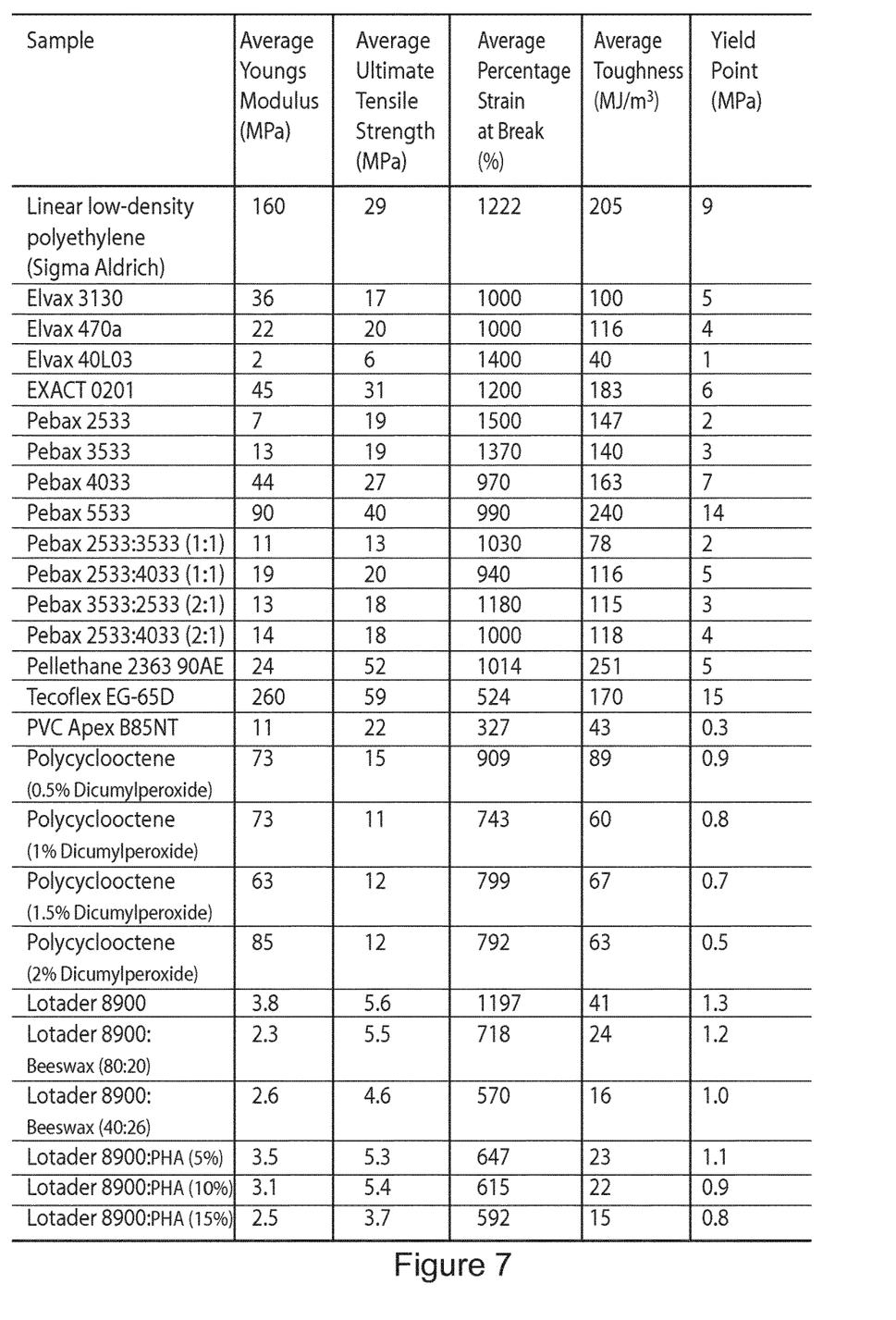
FIG. 7 shows an exemplary table of the properties of different materials which are suitable for use to fabricate the film of the sensor assembly.

In the preferred embodiment of the invention, the polymer material has a characteristically relatively low yield strength (from 1-30 MPa). Additionally the material is tailored to display an extended plastic deformation region under increasing strain without fracture, such that a large portion of the maximum percentage elongation is comprised of irreversible, plastic elongation. FIG. 7 shows an exemplary table of different materials which could be used to fabricate the film, and the experimental results for the values of a number of properties of each of the materials, namely the average young's modulus, the average ultimate tensile strength, the average percentage strain at break, the average toughness and the yield point.

The following are the typical range of these mechanical properties for a suitable film material at room temperature: Young's Modulus: 1-300 MPa, ultimate tensile strength: 1-80 MPa, percentage strain at break: 100→1000, toughness: 5 to 300 $MJ/m^3$ and yield point: 0.01 to 20 MPa. It should be noted that these values relate to both a single and double layer of polymer-based film, without the influence of any external or environmental factors on the polymer-based film.

The top layer 20 and the bottom layer 25 of the polymer film 15 may be bonded by any suitable means, such as chemical adhesion (without our without chemical/mechanical surface priming), heat welding, sonic welding, and light irradiation. The top layer 20 could also be bonded to the bottom layer 25 by any method to cure or partially cure the polymer layer in-situ and exploiting or tailoring surface tension on one or multiple deformable layers. In this regard, it should be noted that for most adhesives, the surface energy of the adhering layer should be the highest in order to achieve optimal adhesive bonding (often >50 dynes/cm). Surface treatments aim to increase the polar portion of the surface free energy which provides active species on the film surface, in order to aid chemical adhesion. Furthermore, by tailoring the surface energy of one or multiple deformable layers, one may cohesively adhere the layers together solely via interatomic interactions, with no use of additional adhesives. This is due to the fact that adhesion and surface energy are directly related, namely adhesion energy (i.e. the energy required to cause fracture) is equal to the surface energy plus additional energy absorbing processes. The top layer 20 could also be bonded to the bottom layer 25 by means of pressure sensitive tack, where a degree of bond is formed between the two layers upon brief contact. This can occur between two materials whose surfaces are tacky to touch (including viscoelastic polymers) via cohesive interaction surface modified to include micro-structured or surface nano-structured topography and/or with an uncross-linked or a lightly cross-linked polymer above the glass transition temperature.

In an alternative embodiment, the components of the sensor assembly are held within a mould, and the stretchable polymer material is flowed into the mould, to envelope and hermetically seal the components. The chemical composition, dimensions and mechanical and rheological properties of this polymer are optimised, such that the film is adequately rigid to allow easy manipulation of the sensor assembly during the splint assembly process and easy configuration to the correct dental arch shape.

The film 15 comprises at least one detachable segment 35. In the described embodiment of the invention, two detachable segments 35 are provided, and these are located in the posterior position of the sensor assembly 1 and are removable without compromising the integrity of the assembly. This enables the device be used in a partially dentate patient. Without this design feature, a full horseshoe shape would only permit use in people who have most or all of their back teeth and would limit the commercial application of the assembly. It will be appreciated that there are several methods that could be used to demarcate the location at which the segments are detachable. These include but are not limited to—a line of perforations, a tear on each side of the perimeter of the polymer film layer, a thinned or crimped area, an area of different and weaker chemical composition, an area highlighted by UV light or physically marked on the film. In its intended use, the wire traversing the separated area would not be cut but safely pulled out from the circuit to avoid contact of an open wire with the external environment. Any local void resulting from the removal of a wire can be filled with a standard filler material, or alternatively be resealed by the application of heat or by the placement of a cap or sheath of thermoplastic polymer over the tern end of the assembly. This overcomes the issue of leaving an exposed wire might affect the performance of the circuit and whole device and compromised safety.

One embodiment of the sensor assembly involves the use of a stretchable pressure sensor where the stretchable sensor material is polymer based. In order to retain electrical contact before and after any stretching of the sensor itself, it is envisaged that the electrode(s) would exist in intimate contact with the sensor in the form of a trellis, wire, mesh or any additional stretchable configurations, which facilities the simultaneous stretching of both the sensor and electrode(s) in a predictable fashion and at the same stretching rate.

In the preferred embodiment of the invention, the electrical resistance of each sensor 5 decreases with increasing externally applied force of a thickness varying from (0.01-3) mm, with the sensor having a shore 'D' hardness ranging from 40-80D.

Each sensor 5 comprises a polymer composite material comprising a polymer mixed with an electrically conductive material. In one embodiment of the invention, the electrically conductive material comprises carbon fibre (20 wt %) added to polyvinyl chloride by means of melt blending. Other suitable electrically conductive materials include metal and carbon-based materials or a combination of both, with dimensions ranging from micron to nanometre. The electrically conductive filler material can take the form of tubes, wires, fibres, spheroids, sheets, beads and matting. The electrically conductive filler material loading ranges from 0.001-50 wt %. In one embodiment of the invention, the final electrically conductive polymer composite film has a resistance at rest of ≥1 MOhms. Under varying applied force, the sensor resistance will decrease in a controlled and reproducible fashion. Accordingly, within the splint or mouth guard, by varying the composition of conductive filler in a pressure sensor film, it allows for the simultaneous detection and heightened sensitivity for both low and high force readings. This allows for sensors of greater sensitivity to be located in certain parts of the mouth as required.

It will be appreciated that the polymer composite material can be prepared by solution or solvent blending, thermal mixing or any standard blending procedure known to one familiar with polymer composite preparation techniques. Each sensor 5 can then be prepared by compression moulding into the desired dimension, or by such techniques including but not limited to wet deposition, thermoforming, extrusion, injection moulding, pultrusion and roll-to-roll deposition.

It should be understood that the values mentioned above are just one example of the values used in a preferred composition of the pressure sensors 5 of the invention. However, any other suitable values could equally well be used. Furthermore, while the preferred embodiment of the invention specifically discusses the sensors response in a PVC or PVDF conductive fibre particle composite system, the composition could alternatively be any intrinsic electrically conductive polymers and piezoelectric polymers and also synthetic (and natural polymer counterpart) elastomer, plastomers, urethane-based, ethylene-based, styrene-based, nylon-based, amide-based, nitrile-based, vinyl-based, propylene-based, acrylic-based and siloxane-based polymer composite systems where the polymer material is mixed with electrically conductive materials.

The sensors 5 are surrounded above and below by a conducting means in the form of a layer of conductive material 40 that connect the sensors 5 to the circuit 10 which transfers and read the output response from the sensors 5 from one form to another. Prior to use, this circuit can be potted or conformally coated and encapsulated in various host matrices including but not limited to thermosetting resins, silicones, polyesters and urethane polymer systems, including all blends and copolymers and with and without addition of standard, known fillers as commonly utilised by those with knowledge of the field. The potting may be done in conjunction with or as a replacement to conformal surface coating.

In an alternative embodiment, there would be one continuous sensor that would be deformed in such a way to customise its shape to the dental arch of the patient. In an alternative embodiment, the stretchable material would form part of the sensing means wherein the bite force activity is detected partly by the plurality of sensors and partly by the deformable layer.

It will be appreciated that the local environment surrounding the sensor assembly 1 can act to dampen or modulate the output signal by absorbing and redistributing a portion of the externally applied force. This local environment includes but is not limited to splint materials above and below the sensor assembly 1, any conformal coating or potting compound near or surrounding the sensors 5, the stretchable polymer film 15 surrounding the sensors 5, any physical recess which is created to aid assembly within a splint, and all required adhesives within this complete assembly. One embodiment of the invention involves the accurate preparation of a recess or cavity within either the hard polymer or soft polymer layer of the dental splint, or both polymer layers simultaneously. This recess would then house the sensor assembly, and all electronics and circuitry required for active function. This recess could be accurately prepared during the thermoforming stage of the dental splint by over moulding a sacrificial and passive layer of defined thickness to replicate the volume required to house the sensor assembly, and all electronics and circuitry required for active function. The sacrificial and passive layer could consist of a foam or sheet of metal or polymer, a pre-prepared wax form of the sensor assembly and/or circuit. The later technique would involve taking an initial impression of the circuit and preparing a wax model for use as a passive layer to form an exact recess in the hard polymer, soft polymer or both splint polymer layers. Techniques such as drilling, abrading, melting, etching, laser removal or other techniques commonly employed by those versed in the knowledge of such preparation may be used for creating a pre-defined shape or housing in a polymer layer.

The present invention also makes use of the material layers of the sensor assembly to optimise the sensor performance. By tailoring the physical and chemical composition of the hermetical seal adhesive or potting compound around the sensors to control their output, the electro-mechanical output, signal quality, signal stability, physical durability or biocompatibility of the sensor assembly may be optimised. Furthermore, by changing the adhesion layer thickness, curing time and viscosity and by matching the shore D hardness of the adhesive compared to that of the sensors and surrounding materials, both the final adhesion layer thickness and the degree to which the adhesive acts as a force dampener can be controlled.

In accordance with the present invention, the circuit 10 includes a data storage means such as memory. The data stored on the memory is transferred by (but not limited to) an infrared transmission protocol to an external device such as a receiver. In one embodiment of the invention, the receiver is integrated within the normal storage cases used for splint storage. The data can then be further transferred from the receiver either wirelessly, or through wired connection to a computer or mobile device and uploaded to a website or application. It could alternatively be relayed directly to a mobile device or directly access a wireless network and be relayed from there to a server for storage and analysis. Software hosted on the website/application or remotely will analyse the data and makes it available to either a dentist or patient in a user-friendly format. The circuit 10 may also include a rechargeable battery.

As previously discussed, the sensor assembly of the present invention is adapted for embedding within a mouth guard or splint. If one were to use the sensor assembly of the invention with a conventional hard/soft splint, by placing the sensor on the trimmed soft layer and thermoforming the hard layer over this layer, prior to bonding the layers together, a number of practical problems would arise. Firstly, the hard and soft layers do not always come together reproducibly, which can be time consuming to correct and result in rough edges. Secondly, the resting pressure between the adhered layers is not predictable, with adverse consequences for circuit functionality and design. This means that each circuit would have to be individually calibrated, as the baseline resistance would be variable and difficult to otherwise interpret. In the setting of a dental practice or routine dental laboratory, this would be beyond the training and skill set of a normally trained person and would not be commercially feasible. Thirdly, there is a considerable shear force between the hard and soft layers when exposed to cyclic loading at high forces. Fourthly, the thickness of the adhesive layer would be unpredictable and likely to be variable leading to sub-optimal adhesion. Fifthly, the joint between the hard and soft layers at the exposed edge is easily accessed and can be deliberately or accidentally separated fairly easily with most adhesives.

Figure 4:
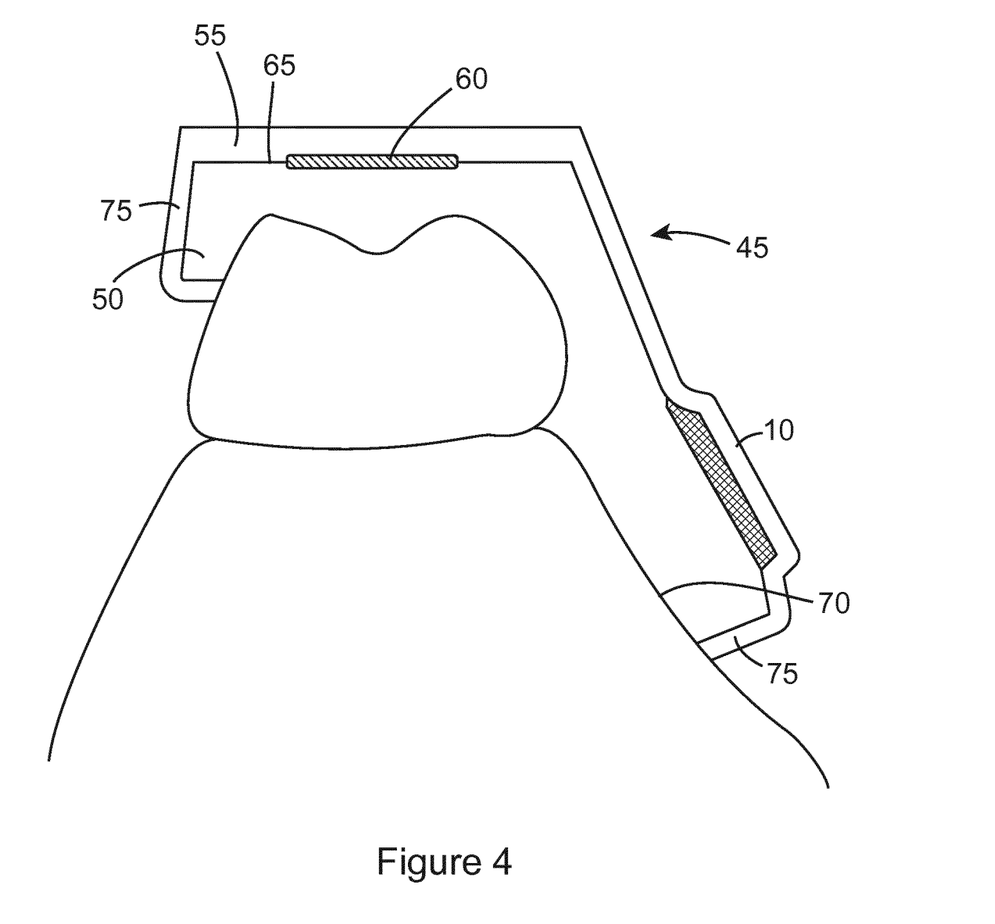
FIG. 4 shows a view of the hard/soft splint of the present invention.

Accordingly, the present invention also provides a hard/soft splint suitable for integration with a sensor such as the sensor assembly of the invention, and adapted to overcome the above mentioned problems. This is achieved by the splint design incorporating a "rim lock" clipping or mating mechanism for coupling the hard layer to the soft layer during the initial assembly of the splint prior to use. This mating mechanism differs from conventional hard/soft splint mating mechanisms where the splint is assembled by simply coupling the hard layer to the top surface of the soft layer, while the side surfaces of the soft layer are left exposed. With the "rim lock" design of the present invention, the hard layer is adapted to be coupled to the soft layer such that the hard layer extends over all surfaces of the soft layer which will not be in direct contact with the teeth of a user. Accordingly, the design provides a lip or rim at the opposing ends of the hard layer which extend over the side surfaces of the soft layer when the hard and soft layers are mated together. As a result, the hard layer and the soft layer can be predictably and easily mated together. Furthermore, once the two layers have been mated or coupled together during initial assembly, the hard layer will remain securely mechanically locked to the soft layer FIG. 4 shows one embodiment of the hard/soft splint 45 of the present invention. It comprises a first layer 50 of soft material comprising a top surface 65, a bottom surface 70 and two side surfaces 75. The bottom surface 70 of the soft layer 50 is for attachment to a first row of teeth when the splint is positioned within the mouth of a user. A second layer 55 of hard material is coupled to the top surface 65 of the soft layer 50 for making contact with a second row of teeth. A sensor 60 is embedded between the hard and soft layers. The "rim lock" design is formed by the hard layer 55 also being coupled to the two side surfaces 75 of the soft layer 50. The hard layer may be coupled to the soft layer by any suitable adhesive means, such as those described previously.

The splint 45 also includes a plurality of grooves placed in one layer while the other layer comprises a plurality of corresponding notches (not shown). The coupling of the grooves to the notches facilitates even more certain and reproducible assembly of the hard and soft layers. However, it will be appreciated that there are many other individual or combinations of physical modification to either layer that could equally achieve the same objective. These include but are not limited to: divets or grooves/slots of any size, depth, number, arrangement or orientation, or corresponding superimposed colour strips on the hard and soft layers, or super imposed notches at the perimeter of both the hard and soft layers.

The hard/soft splint design of the present invention provides numerous advantages over the conventional design of hard/soft splints. By providing an excess of hard layer extending over the perimeter of the soft layer, it provides mechanical bracing that prevents the interfacial movement of the two layers and the resultant shear stress on the adhesive. It also transfers a greater amount of the bite force to the sensor. In addition, it facilitates reproducible reassembly of the mating hard and soft splint layers, and means that any sensor placed in between the hard and soft layers experiences a constant and predictable resting force, and therefore maintains a stable resting resistance. Furthermore, as the joint between the hard and soft layers faces inward, it is considerably more difficult to tear apart or deliberately pick at.

It should be noted that the feasibility of constructing the hard/soft splint so that a sensor such as the sensor assembly of the present invention when integrated into the splint experiences a constant, low and predictable pressure is also heavily influenced by the local environment in between the hard and soft layers of splint material. If the two layers of splint material are made to fit one another without making provision or space in advance for a sensor, the interpositioning of the sensor may prevent the hard and soft layers from coming into intimate contact. It may also result in a high resting force being placed on a sensor, affecting the longevity of the device, and the ease of signal processing and algorithm generation. It is therefore preferable to create a space of adequate and accurate dimensions between the hard and soft layers to house a sensor. One approach to achieve this objective is by recontouring some of the surface of the soft layer, after the hard layer has been overmoulded on the unmodified soft layer. This post fabrication removal of material creates a space for a sensor. However, this process is difficult to perform accurately to by hand, and is thus likely to result in an uneven surface with unpredictable resting resistance.

A preferred approach is therefore is to use a template of the sensor which is to be integrated into the hard/soft splint to create the correct amount of space in advance is of the overmoulding of the hard layer over the soft layer. Once the soft layer is formed and trimmed, the locations where the opposing teeth will contact the hard outer layer of the splint are marked or estimated to determine the correct location of the sensors. A stretchable template of a thermally stable material, of equal dimensions to the sensor can be adhered to the surface of the soft layer in a position that replicates the preferred sensor positioning. The hard layer can then be overmoulded on this, and then the template removed. Through the use of such a template, a recess is formed in the overmoulded hard layer into which the sensor can neatly fit and be subjected to minimal pressure. One embodiment of the invention involves the accurate preparation of a recess or cavity within either the hard polymer or soft polymer layer of the dental splint, or both polymer layers simultaneously. This recess would then house the sensor assembly, and all electronics and circuitry required for active function. This recess could be accurately prepared during the thermoforming stage of the dental splint by over moulding a sacrificial and passive layer of defined thickness to replicate the volume required to house the sensor assembly, and all electronics and circuitry required for active function. The sacrificial and passive layer could consist of a foam or sheet of metal or polymer, a pre-prepared wax form of the sensor assembly and/or circuit.

Hard splints present a whole different set of challenges in order for them to be suitable for integration with sensors such as the sensor assembly of the present invention. In order to embed a sensor in a hard splint, it must either be built into the splint as it is additively constructed using a "salt and pepper" approach, or a space is created in a fully formed splint, with the sensor placed within this created space/cavity and sealed with cold core acrylic. It will be appreciated that arbitrarily creating this cavity by drilling into a fully contoured regular splint or by hand carving the wax template before casting leaves a cavity of uneven dimensions and surface topography. This results in variable depth placement of the sensor relative to the biting surface of the splint, with consequent unpredictability in sensor response and long-term device integrity in areas where the sensor is superficial and the covering acrylic thin.

The present invention therefore also provides a method for fabricating a hard splint suitable for integration with a sensor such as the sensor assembly of the invention, and adapted to overcome the problems described above. The fabrication method can be either physical or by computer modelling. However, both methods use the same principles in order to provide a cavity of uniform dimensions and a smooth surface. This cavity is also predictably located relative to the opposing teeth cusps, to avoid the eccentric contact problems already described.

In the physical method of the invention for fabricating the hard splint, a template of the sensor is integrated into the wax template or model of the hard splint before it is cast. In its simplest form, the method therefore comprises embedding a template for the sensor into a splint template, casting the splint, and removing the sensor template from the cast splint so as to provide a cavity into which the sensor can be embedded.

Figure 5:
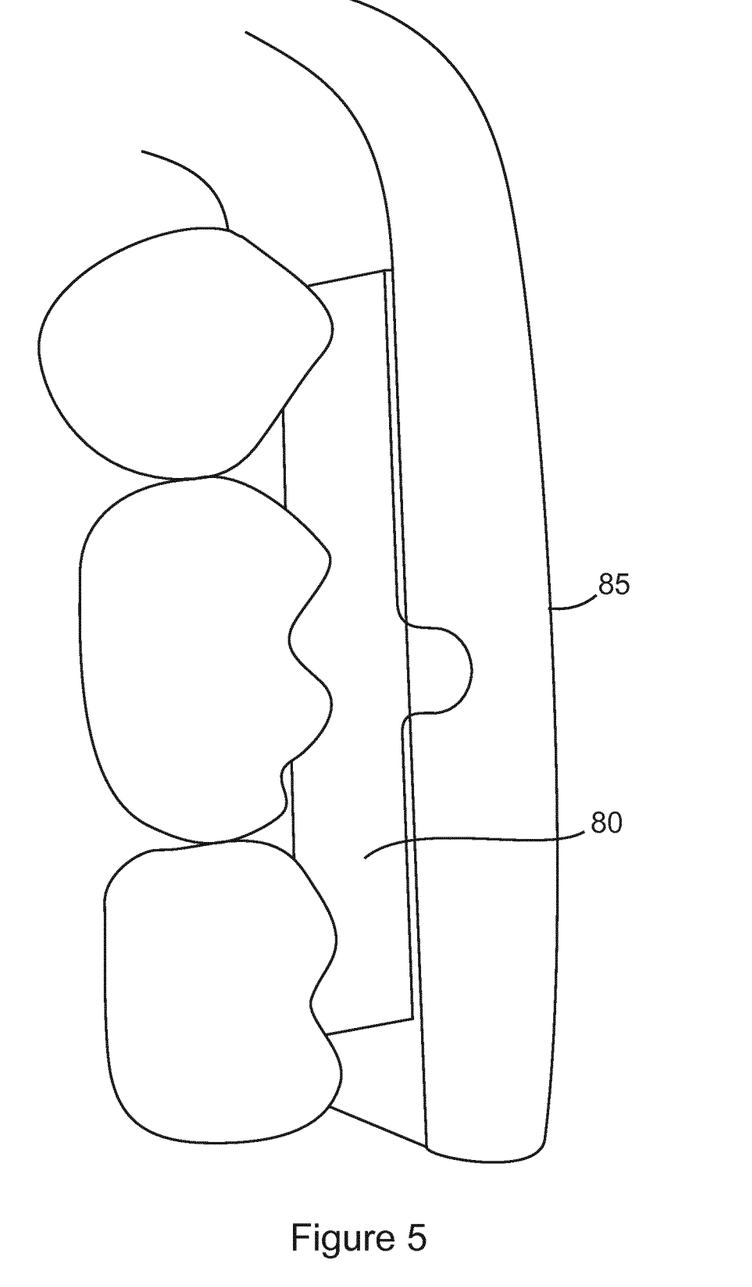
FIG. 5 shows a side view of the sensor template of the present invention embedded in a splint template.
Figure 6:
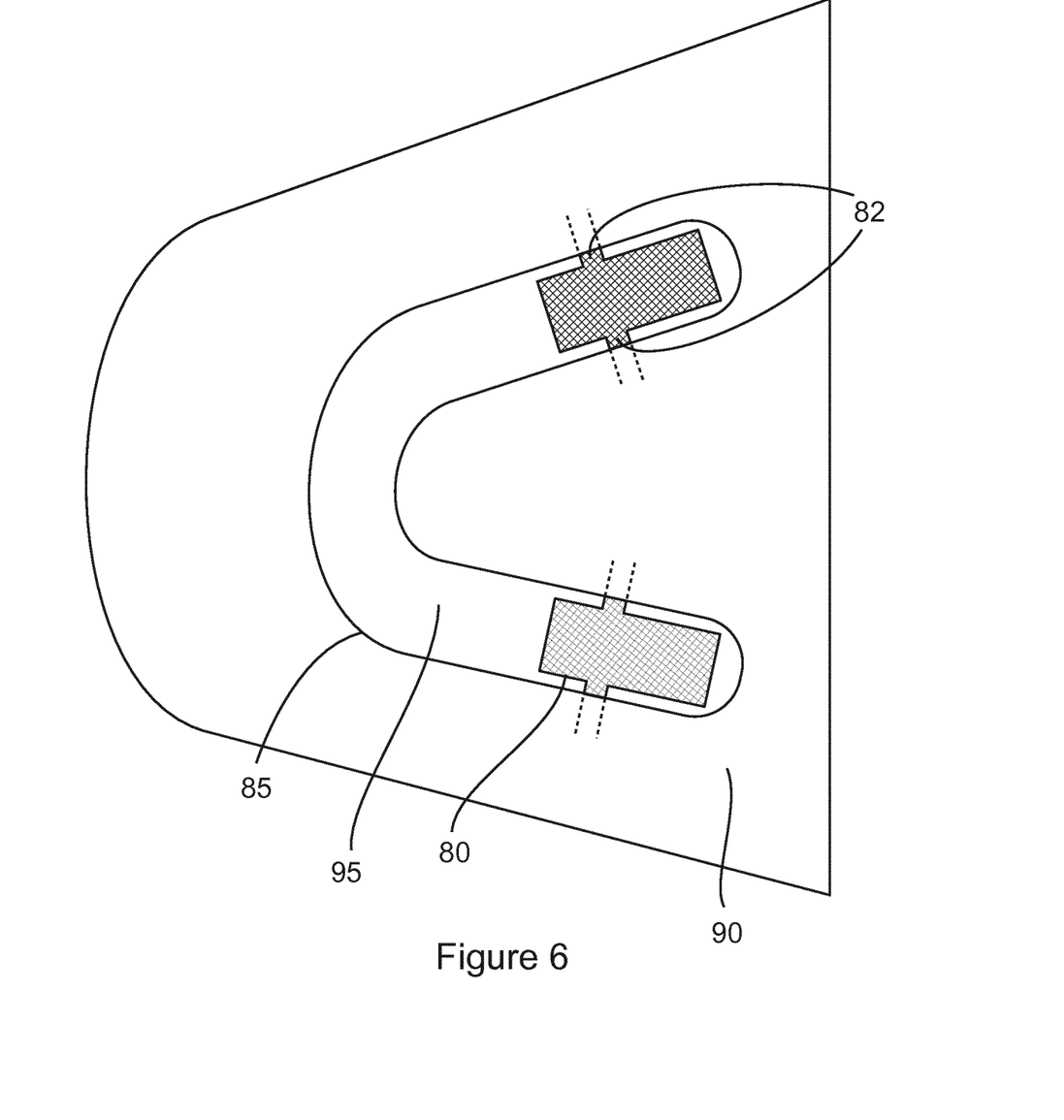
FIG. 6 shows a bottom view of the sensor template of FIG. 5.

As shown in FIGS. 5 and 6, the sensor template 80 is embedded in the splint template 85 such that the exposed surface of the sensor template 80 is aligned with the top surface of the splint template 85, and positioned where the centre of the sensor template 80 is contacted by the opposing teeth on the mounted upper and lower models of the hard splint. Thus, the position of the centre of the sensor template 80 corresponds to where the fabricated splint will make contact with a row of teeth when positioned in a mouth of a user.

The template 80 is dimensioned to be of a similar buccopalatal width as the sensor to be placed in the splint. Accordingly, the templates are of a known and even depth.

The template 80 is also provided with struts or protruding elements 82 that extend out at beyond the occluso-buccal and palatobuccal angles of the splint. In the preferred embodiment of the invention, the protrusions 82 extend out at least 3 mm to beyond these angles.

When the splint 85 has been waxed to full contour, embedded in a stone mould 90 and the wax burned out, the sensor template 80 remains embedded in the mould 90 and the acrylic that is subsequently packed in to the cavity and processed picks up is the negative of the template. In this way, the exact position of the sensor cavity 95 (and therefore the sensor) planned in the wax replica is transferred reliably to the final processed splint. The sensor can then be placed within the cavity 95 and sealed in place with cold cure acrylic or another material.

In the computer or electronic modelling method of the invention for fabricating the hard splint, the fitting and opposing model and the interocclusal record of a mouth are firstly scanned. 3-D electronic models are made of these on a computer program, and the models are electronically articulated. A full contour hard splint is then designed on the electronic model. Once this is done, templates are electronically inserted into the appropriate position on the hard splint image in a corresponding manner to how the template insertion was performed for the fabrication of the physical template described above. The modelling program then electronically removes the template and leaves the correctly sized and located cavity. The physical splint is then either milled from a block of acrylic or manufactured using an additive process such as stereolithography or 3-d printing. The sensor is then placed in the fabricated splint.

While many hard splints are fabricated using a lost wax process, the "salt and pepper" fabrication technique is also still in use. This method involves the hand mixing of small increments of splint material that are applied directly to the surface of a model. The increments gradually build up the splint to shape. This approach to splint fabrication would facilitate the introduction of the sensor assembly of the present invention during the process. For example, initially a base layer of splint material of adequate thickness would be laid down on the model. A dental technician might optionally trim this base layer so that its contour was even. The sensor assembly of the invention would then be adapted or deformed to the ideal size and shape for an individual row of teeth, and secured in place on the base layer. A covering layer of splint material of adequate dimensions would then be placed over the base layer and the sensor assembly, so as to complete the shape of the splint and hermetically seal the sensors.

Another fabrication technique for hard splints uses light/heat cured splint materials. These materials can be used either by direct application to the patient's mouth, or on a model of the patients teeth. The application involving a model of the teeth and the integration of the sensor of the present invention during this process would be conceptually very similar to the salt and pepper technique previously described. For example, a first layer of light/heat curable material would be placed on the model to act as a base, and cured and trimmed to shape. The sensor assembly of the present invention would then be adapted to this base layer and tacked in position. A second layer would then be used to cover the sensor assembly and the first layer, completing the normal splint contour and hermetically sealing the sensor assembly.

In the direct intra-oral application technique, an unpolymerised or partially polymerised layer of material is adapted to the teeth, and partially or fully cured intra-orally. It is retrieved from the mouth and subjected to further curing if required. It is then trimmed to shape. It will be appreciated that integration of the sensor assembly of the present invention into such a splint would require either the embedding of the sensor assembly in the original incompletely polymerised material and direct adaptation to the teeth, or model or, alternatively, the embedding of the sensor assembly between a first and second layer of the light/heat curable material. The intra-oral process would mimic that of the model, except that some initial curing of each layer would occur intra-orally before a possible second definitive cure in a light box or oven or on the benchtop.

It will be appreciated that in order to assess splint compliance and to analyse nightly bruxism data, it is necessary to accurately identify the moment at which the splint is placed in the mouth and removed. The present invention therefore also provides a method for using a characteristic force profile of splint placement and removal to determine the duration of use of the splint. This is facilitated by realisation of the fact that the acts of placing and removing the splint from the mouth delivers a signature pressure sensor characteristic or profile that is very different in intensity, duration and pattern from other bruxism or non-bruxism movements.

In the described embodiment of the invention, the characteristic pattern of the pressure sensor is used to start the nightly recording and to cease it, thereby allowing power management to be more efficient. In this regard, while the splint is located in the base station before use, the circuitry is in a deep sleep mode, consuming tiny amounts of power. The act of placing the splint in the mouth initially wakes the circuit up and puts it in force recording mode. From then on, the sensor will only record and store bite forces that exceed a predefined threshold. If no forces exceed this threshold for a predefined period of time, for example several minutes, the circuit moves into a light sleep mode. In this mode, the circuit consumes very little power but remains vigilant to the input of forces greater than this threshold. If an above threshold force is detected, the circuit wakes up, records the event and stores it in onboard memory for later download. As a result of this process, the circuit conserves power until there is an actual event to record.

The present invention provides a number of advantages over existing products associated with bruxism. Firstly, the invention can be used as a diagnostic tool and/or to monitor bruxism. As a result, it also enables protection of teeth damaged by bruxism to begin while the condition is being monitored. Furthermore, the sensor assembly of the invention can be seamlessly blended into normal splint experience. The inclusion of the sensor assembly within the splint, as well as the data acquisition and transmission hardware within the storage case means that a patient doesn't have to have any extra hardware on their person or at the bedside, and can be easily used by the patient. In addition, as dentists are already familiar with splints, there are low technical or educational barriers to adoption. Furthermore, the design of the sensor assembly ensures that accurate and consistent bruxism data may be collected. Finally, the use of a sensor in a splint is subject to much less setup artefact in the hands of an untrained user such as patients. This is especially the case when compared with EMG based approaches where technique sensitivity can cause significant inconsistency in the recorded signals.

It will be appreciated that while the described embodiments of the invention have focussed on a sensor assembly for use with a splint, a skilled person will understand that the principles of the invention could equally well be applied to any other oral appliance. Furthermore, as mentioned above, the same principles of the invention could be used to monitor other oral conditions other than bruxism. In addition, while the hard/soft splint and hard splint of the present invention have been described for use with a sensor such as the sensor assembly of the present invention, a skilled person will appreciate that these splints could also be used with any other oral appliance.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A sensor assembly for embedding within an oral appliance comprising:
   a sensing means;
   a data processing means coupled to the sensing means for processing data obtained by the sensing means; and
   a conducting means coupling the sensing means to the data processing means;
   wherein the sensing means, the data processing means, and the conducting means are sealed within or positioned on a deformable layer, wherein the sensor assembly is adapted to align the sensing means along different dental arch shapes and sizes by the deformable layer comprising a stretchable film of polymer, by the conducting means being folded in a collapsible arrangement, or by a combination of the deformable layer comprising a stretchable film of polymer and the conducting means being folded in a collapsible arrangement;
   wherein the deformable layer comprises at least one detachable segment located at a posterior position of the sensor assembly and separable from the sensor assembly;
   wherein the at least one detachable segment is separable by a detachment means.

2. The sensor assembly of claim 1, wherein the film is adapted to exhibit a low yield strength and an extended plastic deformation region under increasing strain.

3. The sensor assembly of claim 1, wherein the film is fabricated from one or a combination of: a polyether block amide polymer, polyurethane, polyethylene, polyolefin, polyvinylchloride, polypropylene, polystyrene, elastomer polymer, silicone, terpolymer, reactive polyolefin, plastomer, natural polymer, rubber, biodegradable polymer, biopolymer, inorganic polymer, shape memory polymer, thermoset polymers and a thermoplastic polymer.

4. The sensor assembly of claim 1, wherein the film further comprises additives added to the polymer to control the properties of the film.

5. The sensor assembly of claim 1, wherein the film further comprises additives added to the polymer to control the properties of the film, wherein the additives comprise one or more of: waxes, organic or inorganic clays, organic or inorganic nanotubes, organic or inorganic nanowires, organic or inorganic nanoparticles, organic or inorganic particles, organic or inorganic spheroids, organic or inorganic tubes, organic or inorganic wires, ceramics, organic or inorganic fibres, silica, mica, or glass forms.

6. The sensor assembly of claim 1, wherein the film comprises a top layer and a bottom layer, wherein the sensing means and the data processing means are sealed between the top layer and the bottom layer.

7. The sensor assembly of claim 1, wherein the film comprises a top layer and a bottom layer, wherein the sensing means and the data processing means are sealed between the top layer and the bottom layer, and wherein the top layer is sealed to the bottom layer by one of: chemical adhesion, heat welding, sonic welding, light irradiation, or any method to cure or partially cure the polymer layer in-situ and tailoring surface tension on one or multiple layers, or via pressure sensitive tack where a degree of bond is formed between the two layers upon brief contact.

8. The sensor assembly of claim 1, wherein the sensing means comprises a plurality of pressure sensors for detecting oral pressure activity.

9. The sensor assembly of claim 1, wherein the sensing means comprises a plurality of pressure sensors for detecting oral pressure activity and wherein the deformable layer further defines an indentation between at least two adjacent pressure sensors.

10. The sensor assembly of claim 9, wherein the conducting means is folded in collapsible arrangement around the indentation.

11. The sensor assembly of claim 1, wherein the sensing means comprises a plurality of pressure sensors for detecting oral pressure activity and wherein each pressure sensor comprises:
a polymer composite material comprising a polymer mixed with an electrically conductive material and/or an electrically conductive polymer.

12. The sensor assembly of claim 1, wherein the sensing means comprises a plurality of pressure sensors for detecting oral pressure activity and wherein each pressure sensor has a resistance at rest of >=1 MOhms and a shore hardness within the range of 30D-80D.

13. A splint comprising the sensor assembly of claim 1.

14. A sensor assembly for embedding within an oral appliance comprising:
a sensing means;
a data processing means coupled to the sensing means for processing data obtained by the sensing means; and
a conducting means coupling the sensing means to the data processing means;
wherein the sensing means, the data processing means, and the conducting means are sealed within or positioned on a deformable layer, wherein the sensor assembly is adapted to align the sensing means along different dental arch shapes and sizes by the deformable layer comprising a stretchable film of polymer, by the conducting means being folded in a collapsible arrangement, or by a combination of the deformable layer comprising a stretchable film of polymer and the conducting means being folded in a collapsible arrangement;
wherein the sensing means comprises a plurality of pressure sensors for detecting oral pressure activity;
wherein the deformable layer further defines a plurality of indentations or cut out areas between at least two adjacent pressure sensors;
wherein the plurality of indentations or cut out areas are provided to allow stretch to occur with lower force without the creation of a bump or crease of excess stretched material on the stretchable film.

15. The sensor assembly of claim 14, wherein the film is adapted to exhibit a low yield strength and an extended plastic deformation region under increasing strain.

16. The sensor assembly of claim 14, wherein the film is fabricated from one or a combination of: a polyether block amide polymer, polyurethane, polyethylene, polyolefin, polyvinylchloride, polypropylene, polystyrene, elastomer polymer, silicone, terpolymer, reactive polyolefin, plastomer, natural polymer, rubber, biodegradable polymer, biopolymer, inorganic polymer, shape memory polymer, thermoset polymers and a thermoplastic polymer.

17. The sensor assembly of claim 14, wherein the film further comprises additives added to the polymer to control the properties of the film.

18. The sensor assembly of claim 14, wherein the film further comprises additives added to the polymer to control the properties of the film, wherein the additives comprise one or more of: waxes, organic or inorganic clays, organic or inorganic nanotubes, organic or inorganic nanowires, organic or inorganic nanoparticles, organic or inorganic particles, organic or inorganic spheroids, organic or inorganic tubes, organic or inorganic wires, ceramics, organic or inorganic fibres, silica, mica, or glass forms.

19. The sensor assembly of claim 14, wherein the film comprises a top layer and a bottom layer, wherein the sensing means and the data processing means are sealed between the top layer and the bottom layer.

20. The sensor assembly of claim 14, wherein the film comprises a top layer and a bottom layer, wherein the sensing means and the data processing means are sealed between the top layer and the bottom layer, and wherein the top layer is sealed to the bottom layer by one of: chemical adhesion, heat welding, sonic welding, light irradiation, or any method to cure or partially cure the polymer layer in-situ and tailoring surface tension on one or multiple layers, or via pressure sensitive tack where a degree of bond is formed between the two layers upon brief contact.

21. The sensor assembly of claim 14, wherein the sensing means comprises a plurality of pressure sensors for detecting oral pressure activity and wherein each pressure sensor comprises:
a polymer composite material comprising a polymer mixed with an electrically conductive material and/or an electrically conductive polymer.

22. The sensor assembly of claim 14, wherein the sensing means comprises a plurality of pressure sensors for detecting oral pressure activity and wherein each pressure sensor has a resistance at rest of >=1 MOhms and a shore hardness within the range of 30D-80D.

23. The sensor assembly of claim 14, wherein the deformable layer comprises at least one detachable segment.

24. A splint comprising the sensor assembly of claim 14.

25. The sensor assembly of claim 14, wherein the conducting means is folded in collapsible arrangement around the indentation.

26. A sensor assembly for embedding within an oral appliance comprising:
a sensing means;
a data processing means coupled to the sensing means for processing data obtained by the sensing means; and
a conducting means coupling the sensing means to the data processing means;
wherein the sensing means, the data processing means, and the conducting means are sealed within or positioned on a deformable layer, wherein the sensor assembly is adapted to align the sensing means along different dental arch shapes and sizes by the deformable layer comprising a stretchable film of polymer, by the conducting means being folded in a collapsible arrangement, or by a combination of the deformable layer comprising a stretchable film of polymer and the conducting means being folded in a collapsible arrangement;
wherein the sensing means comprises a plurality of pressure sensors for detecting oral pressure activity;
wherein the deformable layer further defines a plurality of indentations or cut out areas between at least two adjacent pressure sensors;
wherein the plurality of indentations or cut out areas are provided to allow stretch to occur with lower force without the creation of a bump or crease of excess stretched material on the stretchable film;

wherein the deformable layer comprises at least one detachable segment located at a posterior position of the sensor assembly and separable from the sensor assembly;

wherein the at least one detachable segment is separable by a detachment means.

* * * * *